(12) United States Patent
Belanoff

(10) Patent No.: US 8,097,606 B2
(45) Date of Patent: Jan. 17, 2012

(54) ANTIGLUCOCORTICOIDS FOR THE TREATMENT OF CATATONIA

(75) Inventor: Joseph K. Belanoff, Woodside, CA (US)

(73) Assignee: Corcept Therapeutics, Inc., Menlo Park, CA (US)

( * ) Notice: Subject to any disclaimer, the term of this patent is extended or adjusted under 35 U.S.C. 154(b) by 1967 days.

(21) Appl. No.: 10/896,143

(22) Filed: Jul. 20, 2004

(65) Prior Publication Data

US 2005/0080066 A1    Apr. 14, 2005

Related U.S. Application Data

(60) Provisional application No. 60/489,671, filed on Jul. 23, 2003.

(51) Int. Cl.
*A61K 31/56* (2006.01)
(52) U.S. Cl. ........................................................ 514/179
(58) Field of Classification Search .................. 514/179
See application file for complete search history.

(56) References Cited

U.S. PATENT DOCUMENTS

| 5,468,741 | A * | 11/1995 | Yen ............................... 514/179 |
| 5,741,787 | A | 4/1998 | Peeters |
| 6,245,766 | B1 | 6/2001 | Watsky |
| 6,262,042 | B1 | 7/2001 | Cook et al. |
| 6,303,591 | B1 | 10/2001 | Burton et al. |
| 6,362,173 | B1 | 3/2002 | Schatzberg et al. |

FOREIGN PATENT DOCUMENTS

| EP | 1499321 A2 | 1/2005 |
| EP | 1534299 A2 | 6/2005 |
| WO | WO 99/17779 A1 | 4/1999 |
| WO | WO 99/41256 A1 | 8/1999 |
| WO | WO 99/63976 A2 | 12/1999 |
| WO | WO 00/66522 A1 | 11/2000 |
| WO | WO 01/47959 A2 | 7/2001 |
| WO | WO 02/02565 A2 | 1/2002 |
| WO | WO 02/43648 A2 | 6/2002 |
| WO | WO 02/44120 A1 | 6/2002 |
| WO | WO 02/064550 A1 | 8/2002 |
| WO | WO 02/076390 A2 | 10/2002 |
| WO | WO 03/043640 A2 | 5/2003 |
| WO | WO 03/092790 A2 | 11/2003 |
| WO | WO 2004/045653 A2 | 6/2004 |

OTHER PUBLICATIONS

Loose et al. Amer. Society for Clin. Investig. Jul. 1983, vol. 72, pp. 404-408.*
Abravaya, K., et al., "Molecular beacons as diagnostic tools: technology and applications," *Clin Chem Lab Med.*, Apr. 2003, pp. 468-474, vol. 41, No. 4.
Bloodworth, R.C., "The use of the dexamethasone suppression test in the differentia diagnosis of catatonic stupor," *Int. J. Psychiatry Med.*, 1982, pp. 93-101, vol. 12, No. 2.
Hawkins, J.M., et al., "Somatic treatment of catatonia," *Int. J. Psychiatry Med.*, 1995, pp. 345-369, vol. 25, No. 4.
Iwamoto, T., et al., "Loop-Mediated Isothermal Amplification for Direct Detection of Mycobacterium tuberculosis Complex, *M. avium*, and *M. intracellulare* in Sputum Samples," *J. Clin. Microbiol.*, Jun. 2003, pp. 2616-2622, vol. 41, No. 6.
Koenig, J., et al., "Glucocorticoid Hormones and Early Brain Development in Schizophrenia," *Neuropsychopharmacology*, 2002, pp. 309-318, vol. 27.
Lykouras, L., et al., "Clinical subtypes of schizophrenic disorders: a cluster analytic study," *Psychopathology*, Jan. 2001, pp. 23-28, vol. 34, No. 1.
Marco, E.J., et al., "Double-blind antiglucocorticoid treatment in schizophrenia and schizoaffective disorder: a pilot study," *World J. Biol. Psychiatry*, Jul. 2002, pp. 156-161, vol. 3, No. 3.
Taylor, M.A., et al., "Catatonia in psychiatric classification: a home of its own," *Am. J. Psychiatry*, Jul. 2003, pp. 1233-1241, vol. 160, No. 7.
Ungvari, G.S., et al., "The pharmacological treatment of catatonia: an overview," *Eur. Arch. Psychiatry. Clin. Neurosci.*, 2001, vol. 251, Suppl. 1, pp. 131.
Webster, M.J., et al., "Regional specificity of brain glucocorticoid receptor mRNA alterations in subjects with schizophrenia and mood disorders," *Mol. Psychiatry*, 2002, pp. 985-995, 924, vol. 7, No. 9.
Wolkowitz, O.M., et al., "Antiglucocorticoid treatment of depression: double-blind ketoconazole," *Biol. Psychiatry*, Apr. 1999, pp. 1070-1074, vol. 45, No. 8.

* cited by examiner

*Primary Examiner* — Sreeni Padmanabhan
*Assistant Examiner* — Samira Jean-Louis
(74) *Attorney, Agent, or Firm* — Kilpatrick Townsend & Stockton LLP

(57) ABSTRACT

The invention provides a method of ameliorating the symptoms of catatonia in a patient who is in need of treatment for catatonia. The method comprises administration of a therapeutically effective amount of a glucocorticoid receptor antagonist to the patient.

9 Claims, No Drawings

ANTIGLUCOCORTICOIDS FOR THE TREATMENT OF CATATONIA

CROSS-REFERENCES TO RELATED APPLICATIONS

This application claims the benefit under 35 U.S.C. §119(e) of U.S. Provisional Application No. 60/489,671, filed Jul. 23, 2003.

FIELD OF THE INVENTION

This invention generally pertains to the field of psychiatry. In particular, this invention pertains to the discovery that agents which inhibit the biological activity resulting from the binding of cortisol to the glucocorticoid receptor can be used in methods of treating catatonia.

BACKGROUND OF THE INVENTION

Catatonia is a syndrome of motor dysregulation that is found in as many as 10% of acutely ill psychiatric inpatients. According to the DSM IV-TR (*Diagnostic and Statistical Manual of Mental Disorders*, Fourth Edition Text Revision, American Psychiatric Association (2000)) among inpatients with catatonia, 25%-50% of cases occur in association with mood disorders, 10%-15% of cases occur in association with schizophrenia, and the remainder occur in association with other mental disorders such as Obsessive-Compulsive Disorder, Personality Disorders, and Dissociative Disorders. If left untreated, catatonic persons may die of malnutrition and dehydration, or may cause physical harm, including death, to themselves and others.

The most common presentation of catatonia is the retarded—stuporous variety. Catatonic stupor is marked by immobility and a behavior known as waxy flexibility in which the individual can be made to assume bizarre and sometimes painful postures that they will maintain for extended periods of time. Persons experiencing catatonic stupor avoid bathing and grooming, make little or no eye contact with others, may be mute and rigid, and initiate no social behaviors. Besides the possibility of harm and death due to lack of self care, prolonged immobilization during catatonic stupor may lead to life threatening complications such as cachexia (wasting), rhabdomyolysis (muscle destruction), deep venous thrombosis, pulmonary embolism, dehydration, and malnutrition.

Less common, but often more malignant, is the excited—delirious form, sometimes called lethal catatonia, which is characterized by purposeless hyperactivity and violence. The hallmarks of lethal catatonia are acute onset of excitement, delirium, fever, autonomic instability, and catalepsy. The individual may become combative and harm him/herself or others, and in severe end stage cases of excited or lethal catatonia, the person may develop convulsions, coma and even death.

Prompt treatment in the early phases of catatonic states is crucial to obtain a lasting abatement of symptoms. The usual treatments for catatonia include benzodiazapines, supportive care, and electroconvulsive therapy. Unfortunately, the most effective treatments have some disadvantages. For example, when used chronically, benzodiazepines can be addicting, and electroconvulsive therapy remains controversial in its use. Given these drawbacks, there remains a need in the art for a safe, rapid, non-addictive, and effective treatment that can ameliorate the symptoms of catatonia.

Fortunately, the present inventors have determined that glucocorticoid receptor antagonists such as mifepristone are effective agents for the specific treatment of catatonia. Thus the present invention fulfills the need for an effective treatment for the symptoms of catatonia in select patient populations by providing methods of administering glucocorticoid receptor antagonists to treat patients diagnosed with catatonia.

SUMMARY OF THE INVENTION

The invention provides a method of ameliorating the symptoms of catatonia in a patient in need thereof. The method comprises administering an amount of a glucocorticoid receptor antagonist effective to ameliorate the symptoms of catatonia associated with Schizophrenia, Schizoaffective disorder, Obsessive-Compulsive disorder, Personality Disorders and Dissociative Disorders, provided that the patient is not otherwise in need of treatment with a glucocorticoid receptor antagonist. In one embodiment the catatonic disorder is characterized by motoric immobility. In another embodiment, the catatonic disorder is characterized by excessive motor activity.

In one embodiment the glucocorticoid receptor antagonist comprises a steroidal skeleton with at least one phenyl-containing moiety in the 11-beta position of the steroidal skeleton. In a preferred embodiment the phenyl-containing moiety in the 11-beta position of the steroidal skeleton is a dimethylaminophenyl moiety. In another preferred embodiment, the glucocorticoid receptor antagonist comprises mifepristone. In another preferred embodiment, the glucocorticoid receptor antagonist is selected from the group consisting of 11β-(4-dimethylaminoethoxyphenyl)-17α-propynyl-17β-hydroxy-4,9 estradien-3-one and 17β-hydroxy-17α-19-(4-methylphenyl)androsta-4,9(11)-dien-3-one.

In one embodiment the glucocorticoid receptor antagonist is selected from the group consisting 4α(S)-Benzyl-2(R)-prop-1-ynyl-1,2,3,4,4α,9,10,10α(R)-octahydro-phenanthrene-2,7-diol and 4α(S)-Benzyl-2(R)-chloroethynyl-1,2,3,4,4α,9,10,10α(R)-octahydro-phenanthrene-2,7-diol. In another embodiment, the glucocorticoid receptor antagonist is (11β, 17β)-11-(1,3-benzodioxol-5-yl)-17-hydroxy-17-(1-propynyl)estra-4,9-dien-3-one.

In one embodiment, the administration is once per day. In another embodiment, the mode of administration is oral. In another embodiment, the mode of administration is by a transdermal application, by a nebulized suspension, or by an aerosol spray.

The invention also provides a kit for treating catatonia in a human. The kit comprises a specific glucocorticoid receptor antagonist and an instructional material teaching the indications, dosage and schedule of administration of the glucocorticoid receptor antagonist to a patient suffering from catatonia. In one embodiment, the glucocorticoid receptor antagonist is mifepristone. In another embodiment, the mifepristone is in tablet form.

DEFINITIONS

The term "catatonia" or "Catatonic Disorder" refers to a psychological disorder characterized by psychomotor disturbance wherein an individual exhibits catatonic features including motoric immobility, excessive motor activity, extreme negativism, peculiarities of voluntary movement and echolalia or echopraxia. Motoric immobility may be manifest as catalepsy (waxy flexibility) or stupor. The excessive motor activity is apparently purposeless and is not influenced by external stimuli. There may be extreme negativism that is manifest as maintenance of a rigid posture against all attempts to be moved or resistance to all instructions. Peculiarities of voluntary movement may be manifest as voluntary assumption of bizarre postures or prominent grimacing. Echolalia is the pathological, parrotlike repetition of words or phrases just spoken by another person. Echopraxia is the repetitive imitation of the movements of another person. Further clinical manifestations and diagnostic parameters of "catatonia" or "catatonic episodes" are described in detail in the DSM IV-TR (*Diagnostic and Statistical Manual of Mental Disorders*, Fourth Edition Text Revision, American Psychiatric Association (2000)) which is incorporated herein by reference. During severe catatonic stupor or excitement, the person may need careful supervision to avoid self harm or harming of others.

The term "Personality Disorder" refers to any of the ten specific personality disorders listed in the DSM-IV-TR (supra), including: Paranoid Personality Disorder, Schizoid Personality Disorder, Antisocial Personality Disorder, Borderline Personality Disorder, Histrionic Personality Disorder, Narcissistic Personality Disorder, Avoidant Personality Disorder, Dependent Personality Disorder, Obsessive-Compulsive Personality Disorder, and Personality Disorder not otherwise specified. According to the DSM-IV-TR a Personality Disorder is an enduring pattern of inner experience and behavior that deviates markedly from the expectations of the individual's culture and is manifested in at least two of the following areas: cognition, affectivity, interpersonal functioning, or impulse control. The pattern is enduring, inflexible, and pervasive across a broad range of personal and social situations. Diagnosis of a particular Personality Disorder is made in a clinical setting according to the guidelines set forth in the DSM-IV-TR (supra).

The term "Dissociative Disorder" refers to any of the five conditions identified in the DSM-IV-TR as Dissociative Disorders. These include Dissociative Amnesia, Dissociative Fugue, Dissociative Identity disorder, Depersonalization Disorder, and Dissociative Disorder not otherwise specified. The essential feature of Dissociative Disorders is a disruption in the usually integrated functions of consciousness, memory, identity, or perception. The disturbance may be sudden or gradual, transient, or chronic. After ruling out the possibility of an organic illness or medical condition, diagnosis of a particular Dissociative Disorder is made in a clinical setting according to the guidelines set forth in the DSM-IV-TR (supra).

The term "Obsessive-Compulsive Disorder" refers to Obsessive-Compulsive Disorder as described in the DSM-IV-TR. The essential features of Obsessive-Compulsive Disorder are recurrent obsessions or compulsions that are severe enough to be time consuming or cause marked distress or significant impairment. A diagnosis of Obsessive Compulsive Disorder requires the following criteria must be met: 1) the individual experiences recurrent and persistent thoughts, impulses, or images that are intrusive and cause anxiety or distress; 2) the thoughts are not just excessive worries about daily life problems, 3) the individual tries to ignore or suppress the worries with other thoughts, behaviors, or actions aimed at reducing the anxiety or distress, 4) the individual is aware that the thoughts are coming from within their own mind 5) the obsessive-compulsive behaviors last at least 1 hour per day and significantly interfere with the individual's daily routine, 6) the individual is aware that their behavior or thoughts are not rational or are excessive, and 7) the obsessive-compulsive thoughts and behaviors are not due to medications or another medical condition. Further guidelines for the diagnosis of Obsessive-Compulsive Disorder can be found in the DSM-IV-TR (supra).

The term "schizoaffective disorder" refers to schizoaffective disorder as described in the DSM-IV-TR (supra). Schizoaffective Disorder is a disorder in which a mood episode and the active phase symptoms of Schizophrenia occur together, and were preceded or are followed by at least two weeks of delusions and hallucinations without prominent mood symptoms. The essential feature of Schizoaffective Disorder is an uninterrupted period of illness, during which at some time, there is a major depressive, manic, mixed episode, concurrent with symptoms that meet the criteria for schizophrenia. A diagnosis of Schizoaffective Disorder is made in a clinical setting according to the guidelines set forth in the DSM-IV-TR (supra), after ruling out other illnesses or conditions that may produce similar symptoms.

The term "Schizophrenia" refers to schizophrenia as defined in the DSM-IV-TR (supra). The essential features of schizophrenia are a mixture of characteristic signs and symptoms that involve a range of cognitive and emotional dysfunctions that include perception, inferential thinking, language and communication, behavioral monitoring, affect, fluency and productivity of thought and speech, hedonic capacity, volition and drive, and attention. There is no single symptom characteristic of diagnostic of schizophrenia. Rather, the diagnosis involves the recognition of a constellation of signs and symptoms associated with impaired social or occupational functioning. Guidelines for the diagnosis of schizophrenia can be found in DSM-IV-TR (supra).

There are number of different schizophrenic subtypes defined by the predominant symptomology at the time of evaluation. For example, the catatonic type of schizophrenia is characterized by marked psychomotor disturbance, that may involve motoric immobility or excessive motor activity. Other subtypes include paranoid type, disorganized type, residual type and undifferentiated type schizophrenia.

It has been suggested that antiglucocorticoids may be effective for the treatment of schizophrenia. For example, Oberlander WO 98/26785, teaches use of an anti-glucocorticoids to treat schizophrenia and manic states. However, the medical community does not generally accept that antiglucocorticoids are useful for the treatment of schizophrenia, since schizophrenia and manic states are believed to be the result of abnormal nerve structure, rather than the result of a neurochemical (glucocorticoid regulatory) problem. Indeed, although glucocorticoid receptor antagonists have been used to treat the depressive symptoms associated with schizophrenia and schizoaffective disorder (Marco, E. J. et al. (2002) World J. Biol Psychiatry 3(3):156), dopamine and serotonin receptors are the usual targets of anti-schizophrenic drugs. This invention benefits only a subset of schizophrenic patients namely, the population that suffers from catatonia. It is not intended to be general therapeutic for schizophrenia.

A patient "not otherwise in need of treatment with a glucocorticoid receptor antagonist" is a patient who is not being treated with antiglucocorticoid compounds for any disorder accepted by the medical community to be effectively treatable with antiglucocorticoid compounds. Conditions known in the art and accepted by the medical community to be effectively treatable with glucocorticoid receptor antagonists include: Cushing's disease, drug withdrawal, dementia, stress disorders, anxiety disorders (U.S. Pat. No. 5,741,787), depression, psychotic major depression (U.S. Pat. No. 6,150, 349), schizoaffective disorder, diabetes, rheumatoid arthritis, autoimmune disease, HIV infection, dermatitis, inflammation, fibromyalgia, central nervous system disease, neurodegeneration, neural injuries, pelvic pain, and various cancers.

The term "ameliorate" refers to any indicia of success in the treatment of an injury, pathology or condition, including any objective or subjective parameter such as abatement; remission; diminishing of symptoms or making the injury, pathology or condition more tolerable or bearable to the patient; slowing in the rate of degeneration or decline; making the final point of degeneration less debilitating; improving a patient's physical or mental well-being. The amelioration of symptoms can be based on objective or subjective parameters; including the results of a physical examination, neuropsychiatric exams, tests of psychomotor ability, and/or a psychiatric evaluation. For example, the methods of the invention successfully ameliorate a patient's catatonia by decreasing the incidence or severity of psychomotor disturbance. "Ameliorate" as used herein may also mean the complete elimination of the symptoms of catatonia.

The term "cortisol" refers to a family of compositions also referred to as hydrocortisone, and any synthetic or natural analogues thereof.

The term "glucocorticoid receptor" ("GR") refers to a family of intracellular receptors also referred to as the cortisol receptor, which specifically bind to cortisol and/or cortisol analogs. The term includes isoforms of GR, recombinant GR and mutated GR.

The term "mifepristone" refers to a family of compositions also referred to as RU486, or RU38.486, or 17-β-hydroxy-11-β-(4-dimethyl-aminophenyl)-17-α-(1-propynyl)-estra-4,9-dien-3-one), or 11-β-(4dimethylaminophenyl)-17-β-hydroxy-17-α-(1-propynyl)-estra-4,9-dien-3-one), or analogs thereof, which bind to the GR, typically with high affinity, and inhibit the biological effects initiated/mediated by the binding of any cortisol or cortisol analogue to a GR receptor. Chemical names for RU-486 vary; for example, RU486 has also been termed: 11β[p-(Dimethylamino)phenyl]-17β-hydroxy-17-(1-propynyl)-estra-4,9-dien-3-one; 11β-(4-dimethyl-aminophenyl)-17β-hydroxy-17α-(prop-1-ynyl)-estra-4,9-dien-3-one; 17β-hydroxy-11β-(4-dimethylaminophenyl-1)-17α-(propynyl-1)-estra-4,9-diene-3-one; 17β-hydroxy-11β-(4-dimethylaminophenyl-1)-17α-(propynyl-1)-E; (11β,17β)-11-[4-dimethylamino)-phenyl]-17-hydroxy-17-(1-propynyl)estra-4,9-dien-3-one; and 11β-[4-(N,N-dimethylamino)phenyl]-17α-(prop-1-ynyl)-D-4,9-estradiene-17β-ol-3-one.

The term "specific glucocorticoid receptor antagonist" refers to any composition or compound which partially or completely inhibits (antagonizes) the binding of a glucocorticoid receptor (GR) agonist, such as cortisol, or cortisol analogs, synthetic or natural, to a GR. By "specific", we intend the drug to preferentially bind to the GR rather than the mineralocorticoid receptor (MR) with an affinity at least 100-fold, and frequently 1000-fold.

DETAILED DESCRIPTION OF THE INVENTION

Introduction

This invention pertains to the surprising discovery that agents that can inhibit glucocorticoid-induced biological responses are effective for treating catatonia. In treating catatonia, the methods of the invention can ameliorate or preferably eliminate the symptoms of catatonia. In one embodiment, the methods of the invention use agents that act as GR antagonists, blocking the interaction of cortisol with GR, to treat or ameliorate catatonia or symptoms associated with catatonia. The methods of the invention are effective in ameliorating the symptoms of catatonia in an afflicted patient.

Cortisol acts by binding to an intracellular, glucocorticoid receptor (GR). In humans, glucocorticoid receptors are present in two forms: a ligand-binding GR-alpha of 777 amino acids; and, a GR-beta isoform that differs in only the last fifteen amino acids. The two types of GR have high affinity for their specific ligands, and are considered to function through the same transduction pathways.

The biologic effects of cortisol, including pathologies or dysfunctions caused by hypercortisolemia, can be modulated and controlled at the GR level using receptor antagonists. Several different classes of agents are able to act as GR antagonists, i.e., to block the physiologic effects of GR-agonist binding (the natural agonist is cortisol). These antagonists include compositions, which, by binding to GR, block the ability of an agonist to effectively bind to and/or activate the GR. One family of known GR antagonists, mifepristone and related compounds, are effective and potent anti-glucocorticoid agents in humans (Bertagna, *J. Clin. Endocrinol. Metab.* 59:25, 1984). Mifepristone binds to the GR with high affinity, with a K of dissociation<$10^{-9}$ M (Cadepond, *Annu. Rev. Med.* 48:129, 1997). Thus, in one embodiment of the invention, mifepristone and related compounds are used to treat catatonia.

As the methods of the invention include use of any means to inhibit the biological effects of an agonist-bound GR, illustrative compounds and compositions which can be used to treat catatonia are set forth, but these illustrations are not meant to be limiting. Routine procedures that can be used to identify further compounds and compositions able to block the biological response caused by a GR-agonist interaction for use in practicing the methods of the invention are also described. Thus, the specification provides means for identifying compounds suitable for the practice of the invention. As the invention provides for administering these compounds and compositions as pharmaceuticals, routine means to determine GR antagonist drug regimens and formulations to practice the methods of the invention are also set forth below.

1. Diagnosis of Catatonia

Catatonia is characterized by marked motor disturbances that may take the form of motoric immobility, excessive motor activity, extreme negativism, mutism, peculiarities of voluntary movement, echolalia, or echopraxia. Thus, diagnosis of catatonia is made on the basis of specific movement symptoms. In particular, diagnosis of catatonia is made by scoring the number and severity of traits according to the Bush-Francis Catatonia Screening Instrument (BFCSI), or the more expanded, Bush-Francis Catatonia rating Scale (BFCRS, Bush G, et al (1996): Catatonia. I: Rating Scale and Standardized Examination. *Acta Psychiatr Scand* 93:129-136). The presence of any two of the symptoms noted above is sufficient to diagnose catatonia, provided that other causes are ruled out.

A conclusive diagnosis of catatonia also requires knowledge of the patients medical, physical and emotional history so that the presence of non-catatonic disorders such as neuroleptic malignant syndrome, encephalitis, nonconvulsive status epilepticus, and acute psychosis can be ruled out. When appropriate, medical tests such as chemical analysis of blood may be used to rule out infection, trauma, exposure to toxins and other substances which may show some symptoms in common with catatonia.

2. General Laboratory Procedures

When practicing the methods of the invention, a number of general laboratory tests can be used to assist in the diagnosis, progress and prognosis of the patient with catatonia, including monitoring of parameters such as blood cortisol, drug metabolism, brain structure and function and the like. These procedures can be helpful because all patients metabolize and react to drugs uniquely. In addition, such monitoring may be important because each GR antagonist has different pharmacokinetics. Different patients and disease conditions may require different dosage regimens and formulations. Such procedures and means to determine dosage regimens and formulations are well described in the scientific and patent literature. A few illustrative examples are set forth below.

a. Determining Blood Cortisol Levels

Varying levels of blood cortisol have been associated with catatonia, although the invention may also be practiced upon patients with apparently normal levels of blood cortisol. Thus, monitoring blood cortisol and determining baseline cortisol levels are useful laboratory tests to aid in the diagnosis, treatment and prognosis of a catatonia patient. A wide variety of laboratory tests exist that can be used to determine whether an individual is normal, hypo- or hypercortisolemic. Catatonia patients typically have normal levels of cortisol that are often less than 25 µg/dl in the morning, and frequently about 15 µg/dl or less in the afternoon, although the values often fall at the high end of the normal range, which is generally considered to be 5-15 µg/dl in the afternoon.

Immunoassays such as radioimmunoassays are commonly used because they are accurate, easy to do and relatively cheap. Because levels of circulating cortisol are an indicator of adrenocortical function, a variety of stimulation and suppression tests, such as ACTH Stimulation, ACTH Reserve, or dexamethasone suppression (see, e.g., Greenwald, *Am. J. Psychiatry* 143:442-446, 1986), can also provide diagnostic, prognostic or other information to be used adjunctively in the methods of the invention.

One such assay available in kit form is the radioimmunoassay available as "Double Antibody Cortisol Kit" (Diagnostic Products Corporation, Los Angeles, Calif.), (*Acta Psychiatr. Scand* 70:239-247, 1984). This test is a competitive radioimmunoassay in which $^{125}$I-labeled cortisol competes with cortisol from an clinical sample for antibody sites. In this test, due to the specificity of the antibody and lack of any significant protein effect, serum and plasma samples require neither preextraction nor predilution. This assay is described in further detail in Example 2, below.

b. Determination of Blood/Urine Mifepristone Levels

Because a patient's metabolism, clearance rate, toxicity levels, etc. differs with variations in underlying primary or secondary disease conditions, drug history, age, general medical condition and the like, it may be necessary to measure blood and urine levels of GR antagonist. Means for such monitoring are well described in the scientific and patent literature. As in one embodiment of the invention mifepristone is administered to treat catatonia, an illustrative example of determining blood and urine mifepristone levels is set forth in the Example below.

c. Other Laboratory Procedures

Laboratory tests monitoring and measuring GR antagonist metabolite generation, plasma concentrations and clearance rates, including urine concentration of antagonist and metabolites, may also be useful in practicing the methods of the invention. For example, mifepristone has two hydrophilic, N-monomethylated and N-dimethylated, metabolites. Plasma and urine concentrations of these metabolites (in addition to RU486) can be determined using, for example, thin layer chromatography, as described in Kawai *Pharmacol. and Experimental Therapeutics* 241:401-406, 1987.

3. Glucocorticoid Receptor Antagonists to Treat Catatonia

The invention provides for methods of treating catatonia utilizing any composition or compound that can block a biological response associated with the binding of cortisol or a cortisol analogue to a GR. Antagonists of GR activity utilized in the methods of the invention are well described in the scientific and patent literature. A few illustrative examples are set forth below.

A. Steroidal Anti-Glucocorticoids as GR Antagonists.

Steroidal glucocorticoid antagonists are administered to ameliorate the symptoms of catatonia in various embodiments of the invention. Steroidal antiglucocorticoids can be obtained by modification of the basic structure of glucocorticoid agonists, i.e., varied forms of the steroid backbone. The structure of cortisol can be modified in a variety of ways. The two most commonly known classes of structural modifications of the cortisol steroid backbone to create glucocorticoid antagonists include modifications of the 11-beta hydroxy group and modification of the 17-beta side chain (see, e.g., Lefebvre, *J Steroid Biochem.* 33:557-563, 1989).

Examples of steroidal GR antagonists include androgen-type steroid compounds as described in U.S. Pat. No. 5,929, 058, and the compounds disclosed in U.S. Pat. Nos. 4,296, 206; 4,386,085; 4,447,424; 4,477,445; 4,519,946; 4,540,686; 4,547,493; 4,634,695; 4,634,696; 4,753,932; 4,774,236; 4,808,710; 4,814,327; 4,829,060; 4,861,763; 4,912,097; 4,921,638; 4,943,566; 4,954,490; 4,978,657; 5,006,518; 5,043,332; 5,064,822; 5,073,548; 5,089,488; 5,089,635; 5,093,507; 5,095,010; 5,095,129; 5,132,299; 5,166,146; 5,166,199; 5,173,405; 5,276,023; 5,380,839; 5,348,729; 5,426,102; 5,439,913; 5,616,458, 5,696,127, and 6,303,591. Such steroidal GR antagonists include cortexolone, dexamethasone-oxetanone, 19-nordeoxycorticosterone, 19-nor-progesterone, cortisol-21-mesylate; dexamethasone-21-mesylate, 11β-(4-dimethylaminoethoxyphenyl)-17α-propynyl-17β-hydroxy-4,9-estradien-3-one (RU009), and 17β-hydroxy-17α-19-(4-methylphenyl)androsta-4,9(11)-dien-3-one (RU044).

Other examples of steroidal antiglucocorticoids are disclosed in Van Kampen et al. (2002) Eur. J. Pharmacol. 457(2-3):207, WO 03/043640, EP 0 683 172 B1, and EP 0 763 541 B1, each of which is incorporated herein by reference. EP 0 763 541 B1 and Hoyberg et al., *Int'l J. of Neuro-psychopharmacology,* 5:Supp. 1, S148 (2002); disclose the compound (11β,17β)-11-(1,3-benzodioxol-5-yl)-17-hydroxy-17-(1-propynyl)estra-4,9-dien-3-one (ORG 34517) which in a preferred embodiment, is administered in an amount effective to ameliorate or eliminate the symptoms of catatonia.

1. Removal or Substitution of the 11-Beta Hydroxy Group

Glucocorticoid agonists with modified steroidal backbones comprising removal or substitution of the 11-beta hydroxy group are administered in one embodiment of the invention. This class includes natural antiglucocorticoids, including cortexolone, progesterone and testosterone derivatives, and synthetic compositions, such as mifepristone (Lefebvre, et al. supra). Preferred embodiments of the invention include all 11-beta-aryl steroid backbone derivatives because these compounds are devoid of progesterone receptor (PR) binding activity (Agarwal, FEBS 217:221-226, 1987). Another preferred embodiment comprises an 11-beta phenyl-aminodimethyl steroid backbone derivative, i.e., mifepristone, which is both an effective anti-glucocorticoid and anti-progesterone agent. These compositions act as reversibly-binding steroid receptor antagonists. For example, when bound to a 11-beta phenyl-aminodimethyl steroid, the steroid receptor is maintained in a conformation that cannot bind its natural ligand, such as cortisol in the case of GR (Cadepond, 1997, supra).

Synthetic 11-beta phenyl-aminodimethyl steroids include mifepristone, also known as RU486, or 17-beta-hydrox-11-beta-(4-dimethyl-aminophenyl)17-alpha-(1-propynyl)estra-4,9-dien-3-one). Mifepristone has been shown to be a powerful antagonist of both the progesterone and glucocorticoid (GR) receptors. Another 11-beta phenyl-aminodimethyl steroids shown to have GR antagonist effects includes RU009 (RU39.009), 11-beta-(4-dimethyl-aminoethoxyphenyl)-17-alpha-(propynyl-17 beta-hydroxy-4,9-estradien-3-one) (see Bocquel, J. Steroid Biochem. Molec. Biol. 45:205-215, 1993). Another GR antagonist related to RU486 is RU044 (RU43.044) 17-beta-hydrox-17-alpha-19-(4-methyl-phenyl)-androsta-4,9 (11)-dien-3-one) (Bocquel, 1993, supra). See also Teutsch, Steroids 38:651-665, 1981; U.S. Pat. Nos. 4,386,085 and 4,912,097.

One embodiment includes compositions containing the basic glucocorticoid steroid structure which are irreversible anti-glucocorticoids. Such compounds include alpha-ketomethanesulfonate derivatives of cortisol, including cortisol-21-mesylate (4-pregnene-11-beta, 17-alpha, 21-triol-3,20-dione-21-methane-sulfonate and dexamethasone-21-mesylate (16-methyl-9 alpha-fluoro-1,4-pregnadiene-11 beta, 17-alpha, 21-triol-3,20-dione-21-methane-sulfonate). See Simons, J. Steroid Biochem. 24:25-32, 1986; Mercier, J. Steroid Biochem. 25:11-20, 1986; U.S. Pat. No. 4,296,206.

2. Modification of the 17-Beta Side Chain Group

Steroidal antiglucocorticoids which can be obtained by various structural modifications of the 17-beta side chain are also used in the methods of the invention. This class includes synthetic antiglucocorticoids such as dexamethasone-oxetanone, various 17, 21-acetonide derivatives and 17-beta-carboxamide derivatives of dexamethasone (Lefebvre, 1989, supra; Rousseau, Nature 279:158-160, 1979).

3. Other Steroid Backbone Modifications

GR antagonists used in the various embodiments of the invention include any steroid backbone modification which effects a biological response resulting from a GR-agonist interaction. Steroid backbone antagonists can be any natural or synthetic variation of cortisol, such as adrenal steroids missing the C-19 methyl group, such as 19-nordeoxycorticosterone and 19-norprogesterone (Wynne, Endocrinology 107:1278-1280, 1980).

In general, the 11-beta side chain substituent, and particularly the size of that substituent, can play a key role in determining the extent of a steroid's antiglucocorticoid activity. Substitutions in the A ring of the steroid backbone can also be important. 17-hydroxypropenyl side chains generally decrease antiglucocorticoid activity in comparison to 17-propinyl side chain containing compounds.

Additional glucocorticoid receptor antagonists known in the art and suitable for practice of the invention include 21-hydroxy-6,19-oxidoprogesterone (see Vicent, Mol. Pharm. 52:749-753, 1997), Org31710 (see Mizutani, J Steroid Biochem Mol Biol 42(7):695-704, 1992), RU43044, RU40555 (see Kim, J Steroid Biochem Mol Biol. 67(3):213-22, 1998), RU28362, and ZK98299.

B. Non-Steroidal Anti-Glucocorticoids as Antagonists.

Non-steroidal glucocorticoid antagonists are also used in the methods of the invention to ameliorate the symptoms of catatonia in a subject. These include synthetic mimetics and analogs of proteins, including partially peptidic, pseudopeptidic and non-peptidic molecular entities. For example, oligomeric peptidomimetics useful in the invention include (alpha-beta-unsaturated) peptidosulfonamides, N-substituted glycine derivatives, oligo carbamates, oligo urea peptidomimetics, hydrazinopeptides, oligosulfones and the like (see, e.g., Amour, Int. J. Pept. Protein Res. 43:297-304, 1994; de Bont, Bioorganic &Medicinal Chem. 4:667-672, 1996). The creation and simultaneous screening of large libraries of synthetic molecules can be carried out using well-known techniques in combinatorial chemistry, for example, see van Breemen, Anal Chem 69:2159-2164, 1997; and Lam, Anticancer Drug Des 12:145-167, 1997. Design of peptidomimetics specific for GR can be designed using computer programs in conjunction with combinatorial chemistry (combinatorial library) screening approaches (Murray, J. of Computer-Aided Molec. Design 9:381-395, 1995; Bohm, J. of Computer-Aided Molec. Design 10:265-272, 1996). Such "rational drug design" can help develop peptide isomerics and conformers including cycloisomers, retro-inverso isomers, retro isomers and the like (as discussed in Chorev, TibTech 13:438-445, 1995).

Examples of non-steroidal GR antagonists include ketoconazole, clotrimazole; N-(triphenylmethyl)imidazole; N-([2-fluoro-9-phenyl]fluorenyl)imidazole; N-([2-pyridyl] diphenylmethyl)imidazole; N-(2-[4,4',4"-trichlorotrityl]oxyethyl)morpholine; 1-(2[4,4',4"-trichlorotrityl]oxyethyl)-4-(2-hydroxyethyl)piperazine dimaleate; N-([4,4',4"]-trichlorotrityl)imidazole; 9-(3-mercapto-1,2,4-triazolyl)-9-phenyl-2,7-difluorofluorenone; 1-(2-chlorotrityl)-3,5-dimethylpyrazole; 4-(morpholinomethyl)-A-(2-pyridyl) benzhydrol; 5-(5-methoxy-2-(N-methylcarbamoyl)-phenyl) dibenzosuberol; N-(2-chlorotrityl)-L-prolinol acetate; 1-(2-chlorotrityl)-2-methylimidazole; 1-(2-chlorotrityl)-1,2,4-triazole; 1,S-bis(4,4',4"-trichlorotrityl)-1,2,4-triazole-3-thiol; and N-((2,6-dichloro-3-methylphenyl)diphenyl) methylimidazole (see U.S. Pat. No. 6,051,573); the GR antagonist compounds disclosed in U.S. Pat. Nos. 5,696,127 and 6,570.020; the GR antagonist compounds disclosed in US Patent Application 20020077356, the glucocorticoid receptor antagonists disclosed in Bradley et al., J. Med Chem. 45, 2417-2424 (2002), e.g., 4α(S)-Benzyl-2(R)-chloroethynyl-1,2,3,4,4α,9,10,10α(R)-octahydro-phenanthrene-2,7-diol ("CP 394531") and 4α(S)-Benzyl-2(R)-prop-1-ynyl-1,2,3,4,4α,9,10,10α(R)-octahydro-phenanthrene-2,7-diol ("CP 409069") the compounds disclosed in PCT International Application No. WO 96/19458, which describes non-steroidal compounds which are high-affinity, highly selective antagonists for steroid receptors, such as 6-substituted-1,2-dihydro-N-protected-quinolines; and some κ opioid ligands, such as the κ opioid compounds dynorphin-1,13-diamide, U50,488 (trans-(1R,2R)-3,4-dichloro-N-methyl-N-[2-(1-pyrrolidinyl)cyclohexyl]benzeneacetamide), bremazocine and ethylketocyclazocine; and the non-specific opioid receptor ligand, naloxone, as disclosed in Evans et al., Endocrin., 141:2294-2300 (2000).

c. Identifying Specific Glucocorticoid Receptor Antagonists

Because any specific GR antagonist can be used for the treatment of catatonia in the methods of the invention, in addition to the compounds and compositions described above, additional useful GR antagonists can be determined by the skilled artisan. A variety of such routine, well-known methods can be used and are described in the scientific and patent literature. They include in vitro and in vivo assays for the identification of additional GR antagonists. A few illustrative examples are described below.

One assay that can be used to identify a GR antagonist of the invention measures the effect of a putative GR antagonist on tyrosine amino-transferase activity in accordance with the method of Granner, Meth. Enzymol. 15:633, 1970. This analysis is based on measurement of the activity of the liver enzyme tyrosine amino-transferase (TAT) in cultures of rat hepatoma cells (RHC). TAT catalyzes the first step in the metabolism of tyrosine and is induced by glucocorticoids (cortisol) both in liver and hepatoma cells. This activity is easily measured in cell extracts. TAT converts the amino group of tyrosine to 2-oxoglutaric acid. P-hydroxyphenylpyruvate is also formed. It can be converted to the more stable p-hydroxybenzaldehyde in an alkaline solution and quantitated by absorbance at 331 nm. The putative GR antagonist is co-administered with cortisol to whole liver, in vivo or ex vivo, or hepatoma cells or cell extracts. A compound is identified as a GR antagonist when its administration decreases the amount of induced TAT activity, as compared to control (i.e., only cortisol or GR agonist added) (see also Shirwany, *Biochem. Biophys. Acta* 886:162-168, 1986).

Further illustrative of the many assays which can be used to identify compositions utilized in the methods of the invention, in addition to the TAT assay, are assays based on glucocorticoid activities in vivo. For example, assays that assess the ability of a putative GR antagonist to inhibit uptake of $^3$H-thymidine into DNA in cells which are stimulated by glucocorticoids can be used. Alternatively, the putative GR antagonist can complete with $^3$H-dexamethasone for binding to a hepatoma tissue culture GR (see, e.g., Choi, et al., *Steroids* 57:313-318, 1992). As another example, the ability of a putative GR antagonist to block nuclear binding of $^3$H-dexamethasone-GR complex can be used (Alexandrova et al., *J. Steroid Biochem. Mol. Biol.* 41:723-725, 1992). To further identify putative GR antagonists, kinetic assays able to discriminate between glucocorticoid agonists and antagonists by means of receptor-binding kinetics can also be used (as described in Jones, *Biochem J.* 204:721-729, 1982).

In another illustrative example, the assay described by Daune, *Molec. Pharm.* 13:948-955, 1977; and in U.S. Pat. No. 4,386,085, can be used to identify anti-glucocorticoid activity. Briefly, the thymocytes of adrenalectomized rats are incubated in nutritive medium containing dexamethasone with the test compound (the putative GR antagonist) at varying concentrations. $^3$H-uridine is added to the cell culture, which is further incubated, and the extent of incorporation of radiolabel into polynucleotide is measured. Glucocorticoid agonists decrease the amount of $^3$H-uridine incorporated. Thus, a GR antagonist will oppose this effect.

For additional compounds that can be utilized in the methods of the invention and methods of identifying and making such compounds, see U.S. Pat. Nos. 4,296,206 (see above); 4,386,085 (see above); 4,447,424; 4,477,445; 4,519,946; 4,540,686; 4,547,493; 4,634,695; 4,634,696; 4,753,932; 4,774,236; 4,808,710; 4,814,327; 4,829,060; 4,861,763; 4,912,097; 4,921,638; 4,943,566; 4,954,490; 4,978,657; 5,006,518; 5,043,332; 5,064,822; 5,073,548; 5,089,488; 5,089,635; 5,093,507; 5,095,010; 5,095,129; 5,132,299; 5,166,146; 5,166,199; 5,173,405; 5,276,023; 5,380,839; 5,348,729; 5,426,102; 5,439,913; and 5,616,458; and WO 96/19458, which describes non-steroidal compounds which are high-affinity, highly selective modulators (antagonists) for steroid receptors, such as 6-substituted-1,2-dihydro N-1 protected quinolines.

The specificity of the antagonist for the GR relative to the MR can be measured using a variety of assays known to those of skill in the art. For example, specific antagonists can be identified by measuring the ability of the antagonist to bind to the GR compared to the MR (see, e.g., U.S. Pat. Nos. 5,606, 021; 5,696,127; 5,215,916; 5,071,773). Such an analysis can be performed using either direct binding assay or by assessing competitive binding to the purified GR or MR in the presence of a known antagonist. In an exemplary assay, cells that are stably expressing the glucocorticoid receptor or mineralocorticoid receptor (see, e.g., U.S. Pat. No. 5,606,021) at high levels are used as a source of purified receptor. The affinity of the antagonist for the receptor is then directly measured. Those antagonists that exhibit at least a 100-fold higher affinity, often 1000-fold, for the GR relative to the MR are then selected for use in the methods of the invention.

A GR-specific antagonist may also be defined as a compound that has the ability to inhibit GR-mediated activities, but not MR-mediated activities. One method of identifying such a GR-specific antagonist is to assess the ability of an antagonist to prevent activation of reporter constructs using transfection assays (see, e.g., Bocquel et al, *J. Steroid Biochem Molec. Biol.* 45:205-215, 1993, U.S. Pat. Nos. 5,606, 021, 5,929,058). In an exemplary transfection assay, an expression plasmid encoding the receptor and a reporter plasmid containing a reporter gene linked to receptor-specific regulatory elements are cotransfected into suitable receptor-negative host cells. The transfected host cells are then cultured in the presence and absence of a hormone, such as cortisol or analog thereof, able to activate the hormone responsive promoter/enhancer element of the reporter plasmid. Next the transfected and cultured host cells are monitored for induction (i.e., the presence) of the product of the reporter gene sequence. Finally, the expression and/or steroid binding-capacity of the hormone receptor protein (coded for by the receptor DNA sequence on the expression plasmid and produced in the transfected and cultured host cells), is measured by determining the activity of the reporter gene in the presence and absence of an antagonist. The antagonist activity of a compound may be determined in comparison to known antagonists of the GR and MR receptors (see, e.g., U.S. Pat. No. 5,696,127). Efficacy is then reported as the percent maximal response observed for each compound relative to a reference antagonist compound. A GR-specific antagonist is considered to exhibit at least a 100-fold, often 1000-fold or greater, activity towards the GR relative to the MR.

4. Treatment of Catatonia Using Glucocorticoid Receptor Antagonists

Antiglucocorticoids, such as mifepristone, are formulated as pharmaceuticals to be used in the methods of the invention to treat catatonia. Any composition or compound that can block a biological response associated with the binding of cortisol or a cortisol analogue to a GR can be used as a pharmaceutical in the invention. Routine means to determine GR antagonist drug regimens and formulations to practice the methods of the invention are well described in the patent and scientific literature, and some illustrative examples are set forth below.

a. Glucocorticoid Receptor Antagonists as Pharmaceutical Compositions

The GR antagonists used in the methods of the invention can be administered by any means known in the art, e.g., parenterally, topically, orally, or by local administration, such as by aerosol or transdermally. The methods of the invention provide for prophylactic and/or therapeutic treatments. The GR antagonists as pharmaceutical formulations can be administered in a variety of unit dosage forms depending upon the condition or disease and the degree of catatonia, the general medical condition of each patient, the resulting preferred method of administration and the like. Details on techniques for formulation and administration are well described in the scientific and patent literature, see, e.g., the latest edition of Remington's Pharmaceutical Sciences, Maack Publishing Co, Easton Pa. ("Remington's").

GR antagonist pharmaceutical formulations can be prepared according to any method known to the art for the manufacture of pharmaceuticals. Such drugs can contain sweetening agents, flavoring agents, coloring agents and preserving agents. Any GR antagonist formulation can be admixtured with nontoxic pharmaceutically acceptable excipients which are suitable for manufacture.

Pharmaceutical formulations for oral administration can be formulated using pharmaceutically acceptable carriers well known in the art in appropriate and suitable dosages. Such carriers enable the pharmaceutical formulations to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be obtained through combination of GR antagonist compounds with a solid excipient, optionally grinding a resulting mixture, and processing the mixture of granules, after adding suitable additional compounds, if desired, to obtain tablets or dragee cores. Suitable solid excipients are carbohydrate or protein fillers include, but are not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain GR antagonist mixed with a filler or binders such as lactose or starches, lubricants such as talc or magnesium stearate, and, optionally, stabilizers. In soft capsules, the GR antagonist compounds may be dissolved or suspended in suitable liquids, such as fatty oils, liquid paraffin, or liquid polyethylene glycol with or without stabilizers.

Aqueous suspensions of the invention contain a GR antagonist in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending a GR antagonist in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

Dispersible powders and granules of the invention suitable for preparation of an aqueous suspension by the addition of water can be formulated from a GR antagonist in admixture with a dispersing, suspending and/or wetting agent, and one or more preservatives. Suitable dispersing or wetting agents and suspending agents are exemplified by those disclosed above. Additional excipients, for example, sweetening, flavoring and coloring agents, can also be present.

The GR antagonists of this invention can also be administered in the form of suppositories for rectal administration of the drug. These formulations can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

The GR antagonists of this invention can also be administered by in intranasal, intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995).

The GR antagonists of the invention can be delivered by transdermally, by a topical route, formulated as applicator sticks, solutions, suspensions, emulsions, gels, creams, ointments, pastes, jellies, paints, powders, and aerosols.

The GR antagonists of the invention can also be delivered as microspheres for slow release in the body. For example, microspheres can be administered via intradermal injection of drug (e.g., mifepristone)-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

The GR antagonist pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5, that is combined with buffer prior to use.

In another embodiment, the GR antagonist formulations of the invention are useful for parenteral administration, such as intravenous (IV) administration or administration into a body cavity or lumen of an organ. The formulations for administration will commonly comprise a solution of the GR antagonist (e.g., mifepristone) dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of GR antagonist in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the GR antagonist formulations of the invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the GR antagonist into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

b. Determining Dosing Regimens for Glucocorticoid Receptor Antagonists

The methods of the invention treat catatonia, i.e., reduce the incidence and severity of motor disturbance and movement symptoms that may take the form of motoric immobility, excessive motor activity, extreme negativism, mutism, peculiarities of voluntary movement, echolalia, echopraxia, or other characteristic catatonic symptoms. The amount of GR antagonist adequate to accomplish this is defined as a "therapeutically effective dose". The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the GR antagonists' rate of absorption, bioavailability, metabolism, clearance, and the like (see, e.g., Hidalgo-Aragones (1996) *J. Steroid Biochem. Mol. Biol.* 58:611-617; Groning (1996) *Pharmazie* 51:337-341; Fotherby (1996) *Contraception* 54:59-69; Johnson (1995) *J. Pharm. Sci.* 84:1144-1146; Rohatagi (1995) *Pharmazie* 50:610-613; Brophy (1983) *Eur. J. Clin. Pharmacol.* 24:103-108; the latest Remington's, supra). For example, in one study, less than 0.5% of the daily dose of mifepristone was excreted in the urine; the drug bound extensively to circulating albumin (see Kawai (1989) supra). The state of the art allows the clinician to determine the dosage regimen for each individual patient, GR antagonist and disease or condition treated. As an illustrative example, the guidelines provided below for mifepristone can be used as guidance to determine the dosage regimen, i.e., dose schedule and dosage levels, of any GR antagonist administered when practicing the methods of the invention.

Single or multiple administrations of GR antagonist formulations can be administered depending on the dosage and frequency as required and tolerated by the patient. The formulations should provide a sufficient quantity of active agent, i.e., mifepristone, to effectively treat the catatonia. Thus, one typical pharmaceutical formulations for oral administration of mifepristone is in a daily amount of between about 0.5 to about 20 mg per kilogram of body weight per day. In an alternative embodiment, dosages are from about 1 mg to about 4 mg per kg of body weight per patient per day are used. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing parenterally administrable GR antagonist formulations will be known or apparent to those skilled in the art and are described in more detail in such publications as Remington's, supra. See also Nieman, In "Receptor Mediated Antisteroid Action," Agarwal, et al., eds., De Gruyter, N.Y. (1987).

After a pharmaceutical comprising a GR antagonist of the invention has been formulated in a acceptable carrier, it can be placed in an appropriate container and labeled for treatment of an indicated condition. For administration of GR antagonists, such labeling would include, e.g., instructions concerning the amount, frequency and method of administration. In one embodiment, the invention provides for a kit for the treatment of catatonia in a human which includes a GR antagonist and instructional material teaching the indications, dosage and schedule of administration of the GR antagonist.

EXAMPLES

The following examples are offered to illustrate, but not to limit the claimed invention.

Example 1

Treating Catatonia with Mifepristone

The following example demonstrates how to practice the methods of the invention.

Patient Selection

Individuals are diagnosed with catatonia using subjective and objective criteria, including criteria as set forth by the DSM-IV-TR, and the Bush-Francis Catatonia Screening Instrument (BFCSI), or the more expanded, Bush-Francis Catatonia rating Scale (BFCRS, Bush G, et al (1996): Catatonia. I: Rating Scale and Standardized Examination. *Acta Psychiatr Scand* 93:129-136). The catatonia patient typically has normal levels of cortisol for his or her age.

Dosage Regimen and Administration of Mifepristone

The glucocorticoid receptor (GR) antagonist, mifepristone, is used in this study. It is administered in dosages of 600 mg daily. Individuals will be given 600 mg of mifepristone daily for six days and evaluated as described below. Dosages will be adjusted if necessary and further evaluations will be performed periodically throughout treatment. Mifepristone tablets are available from Shanghai HuaLian Pharmaceuticals Co., Ltd., Shanghai, China.

Assessing Treatment of Catatonia

Since catatonia is a syndrome characterized by the presence of a variety of behavioral and motoric traits, assessing the effectiveness of mifepristone in ameliorating the symptoms of catatonia, is made by scoring the number and severity of traits according to the Bush-Francis Catatonia Screening Instrument (BFCSI), or the Bush-Francis Catatonia rating Scale (BFCRS) as noted above. The patients' score according to these standardized rating scales will take place at baseline (patient's entry into treatment) and periodically throughout treatment. Improvement is indicated by at least a 5% change in the in the patient's BFCRS score over the course of treatment.

Example 2

Measuring Cortisol Levels

To measure cortisol levels of the patients of Example 1, afternoon Cortisol Test measurements are taken and used as the baseline cortisol measure. Cortisol levels are taken at Day 0, and at two weeks after receiving the medication (Day 14).

The "Double Antibody Cortisol Kit" (Diagnostic Products Corporation, Los Angeles, Calif.) is used to measure blood cortisol levels. This test is a competitive radioimmunoassay in which $^{125}$I-labeled cortisol competes with cortisol from an clinical sample for antibody sites, and is performed essentially according to manufacturer's instructions using reagents supplied by manufacturer. Briefly, blood is collected by venipuncture and serum separated from the cells. The samples are stored at 2 to 8° C. for up to seven days, or up to two month frozen at −20° C. Before the assay, samples are allowed to come up to room temperature (15-28° C.) by gentle swirling or inversion. Sixteen tubes in duplicate at 25 microliters of serum per tube are prepared. Cortisol concentrations is calculated from the prepared calibration tubes. Net counts equals the average CPM minus the average non-specific CPM. Cortisol concentrations for the unknowns is estimated by interpolation from the calibration curve (Dudley, et al. (1985) Clin. Chem. 31:1264-1271).

It is understood that the examples and embodiments described herein are for illustrative purposes only and that various modifications or changes in light thereof will be suggested to persons skilled in the art and are to be included within the spirit and purview of this application and scope of the claims.

What is claimed is:

1. A method of ameliorating the symptoms of catatonia in a patient in need thereof, comprising administering an amount of a specific glucocorticoid receptor antagonist effective to ameliorate the symptoms of the catatonia, wherein
the catatonia is associated with a mental disorder selected from the group consisting of: Schizophrenia, Schizoaffective disorder, Obsessive-Compulsive Disorder, a Personality Disorder and a Dissociative Disorder, and
with the proviso that the patient is not otherwise in need of treatment with a specific glucocorticoid receptor antagonist.

2. The method of claim 1, wherein the catatonia is characterized by motoric immobility.

3. The method of claim 1, wherein the catatonia is characterized by excessive motor activity.

4. The method of claim 1, wherein the glucocorticoid receptor antagonist comprises a steroidal skeleton with at least one phenyl-containing moiety in the 11-beta position of the steroidal skeleton.

5. The method of claim 4, wherein the phenyl-containing moiety in the 11-beta position of the steroidal skeleton is a dimethylaminophenyl moiety.

6. The method of claim 5, wherein the glucocorticoid receptor antagonist is mifepristone.

7. The method of claim 1, wherein the administration is once per day.

8. The method of 1, wherein the mode of administration is oral.

9. The method of claim 1, wherein the mode of administration is by a transdermal application, by a nebulized suspension, or by an aerosol spray.

* * * * *